US00PP31995P2

(12) United States Plant Patent
Yanny

(10) Patent No.: US PP31,995 P2
(45) Date of Patent: Jul. 21, 2020

(54) ***SPIRAEA* PLANT NAMED 'JN SELECT J'**

(50) Latin Name: ***Spiraea* hybrid**
Varietal Denomination: JN Select J

(71) Applicant: Michael D. Yanny, Milwaukee, WI (US)

(72) Inventor: Michael D. Yanny, Milwaukee, WI (US)

(73) Assignee: JN PLANT SELECTIONS, LLC, Milwaukee, WI (US)

( * ) Notice: Subject to any disclaimer, the term of this patent is extended or adjusted under 35 U.S.C. 154(b) by 0 days.

(21) Appl. No.: 16/602,374

(22) Filed: Sep. 25, 2019

(51) Int. Cl.
*A01H 5/02* (2018.01)
*A01H 6/74* (2018.01)

(52) U.S. Cl.
USPC ..... Plt./226
CPC ..... *A01H 6/74* (2018.05)

(58) Field of Classification Search
USPC ..... Plt./226
CPC ..... A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of *Spiraea* plant named 'JN Select J' that is characterized by its red to maroon splotches on leaves that intensify in summer into autumn, its consistent red fall foliage coloration, its flowers that are pink in color, its large plant size, and its lack of seed production.

2 Drawing Sheets

Botanical classification: *Spiraea* hybrid.
Variety denomination: 'JN Select J'.

BACKGROUND OF THE INVENTION

The present invention relates to a new and distinct cultivar known as *Spiraea* 'JN Select J' and referred to hereafter by its cultivar name, 'JN Select J'. 'JN Select J' is a new variety of *Spiraea* grown for use as a landscape plant.

'JN Select J' was discovered by the Inventor as a chance seedling by the Inventor in a production field in Menomonee Falls, Wis. in October of 2004. The field had been planted with seedlings of seeds collected from an open pollinated plant of an unnamed and unpatented plant of *Spiraea fritschiana*. The exact male parent is unknown; however, it is most likely *Spiraea* x *bumalda* 'Norman' (not patented) based on its characteristics and its proximity to the new cultivar (growing 50 feet from the plants that seeds were collected from).

Asexual propagation of the new cultivar was first accomplished by the Inventor by softwood stem cuttings in June of 2005 in Menomonee Falls, Wis. Asexual propagation of the new cultivar by softwood stem cuttings has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'JN Select J' as a new and unique cultivar of *Spiraea*.

1. 'JN Select J' exhibits red to maroon splotches on leaves that intensify in summer into autumn.
2. 'JN Select J' exhibits consistent red fall foliage coloration.
3. 'JN Select J' exhibits flowers that are pink in color.

4. 'JN Select J' exhibits a large plant size; reaching 1.07 m in height by 1.52 m in width.
5. 'JN Select J' exhibits no seed production.

The female parent of 'JN Select J' differs from 'JN Select J' in having leaves that lack red-maroon color splotches, yellow foliage color in the fall, flowers that are white in color and in being highly fertile; producing an abundance of seed. The probable male parent of 'JN Select J', 'Norman', differs from 'JN Select J' in having leaves that lacks red-maroon colored splotches, maroon leaf color in fall, a shorter plant height and in being highly fertile; producing an abundance of seed. 'JN Select J' can also be most closely compared to the *Spiraea fritschiana* cultivar 'JN Select A' (not patented) and *Spiraea* x *bumalda* cultivar 'Froebelii' (not patented). 'JN Select A' is similar to 'JN Select J' in lacking seed production. 'JN Select A' differs from 'JN Select J' in having leaves that lack red-maroon colored splotches, a mix of yellow, apricot and pink fall foliage coloration, and a smaller plant height and width. 'Froebelii' is similar to 'JN Select J' in having flowers that are similar in size and color and consistent fall foliage coloration. 'Froebelii' differs from 'JN Select J' in having leaves that lack red-maroon colored splotches, purple-maroon fall foliage color, flowers that are darker pink in color, and in being highly fertile; producing an abundance of seed.

BRIEF DESCRIPTION OF THE DRAWINGS

The accompanying colored photographs illustrate the overall appearance and distinct characteristics of the new *Spiraea*. The photographs were taken of the plant as grown outdoors in a field in Menomonee Falls, Wis.

The photograph in FIG. 1 provides a view of a 12-year-old plant of 'JN Select J' in bloom.

Figure 1:
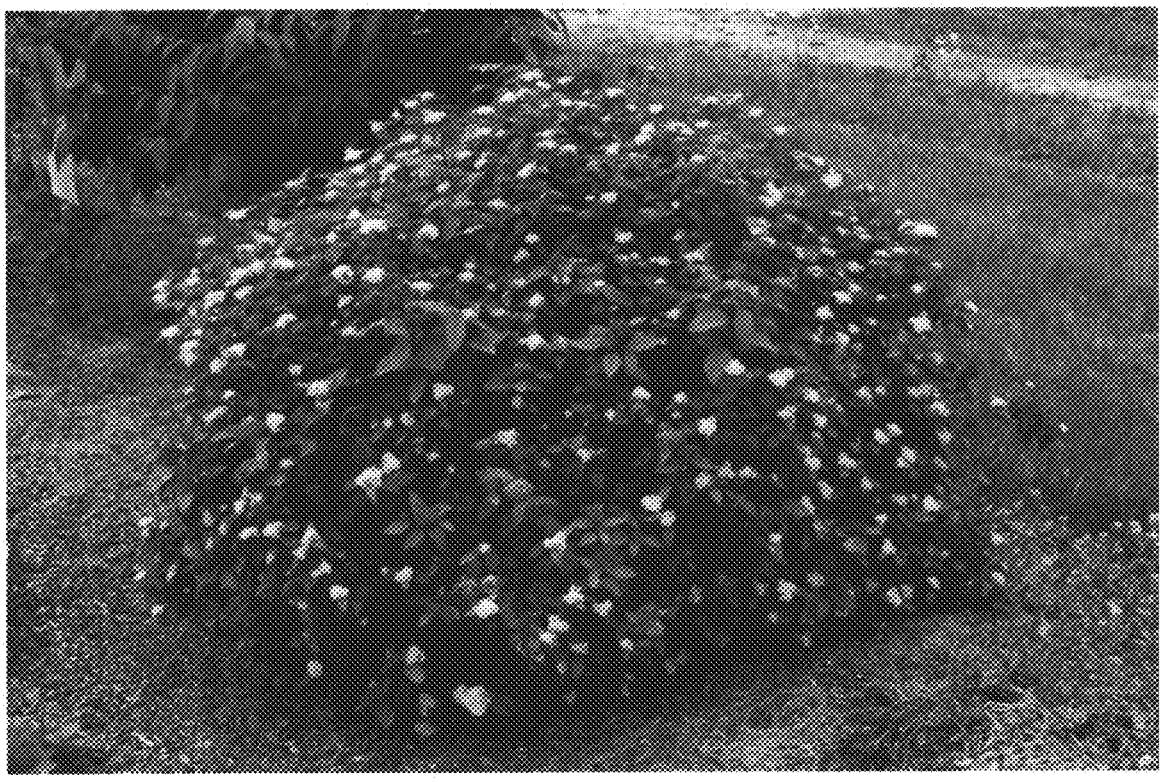
Figure 2:
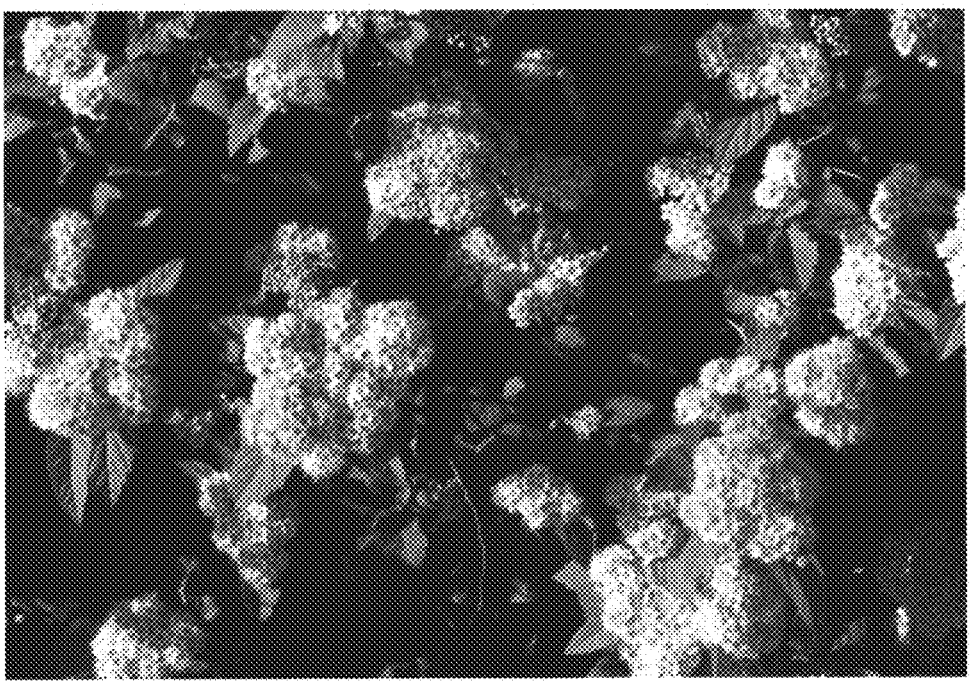

The photograph in FIG. 2 provides a close-up view of the inflorescences of a 10-year-old plant of 'JN Select J'.

Figure 3:
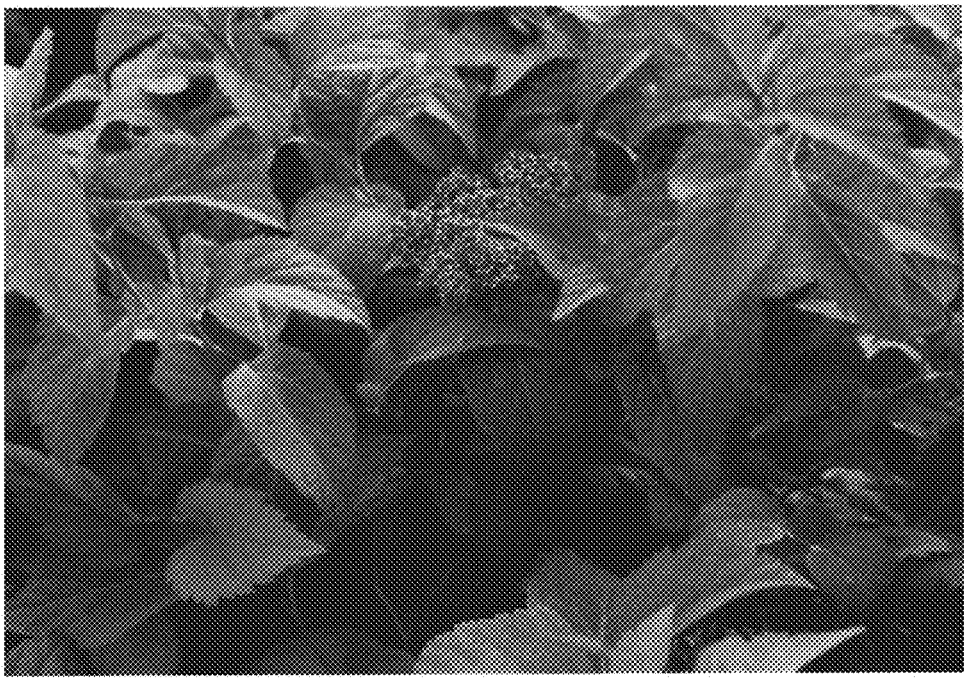

The photograph in FIG. 3 provides a close-up view of the foliage of a 5-year-old plant of 'JN Select J'.

Figure 4:
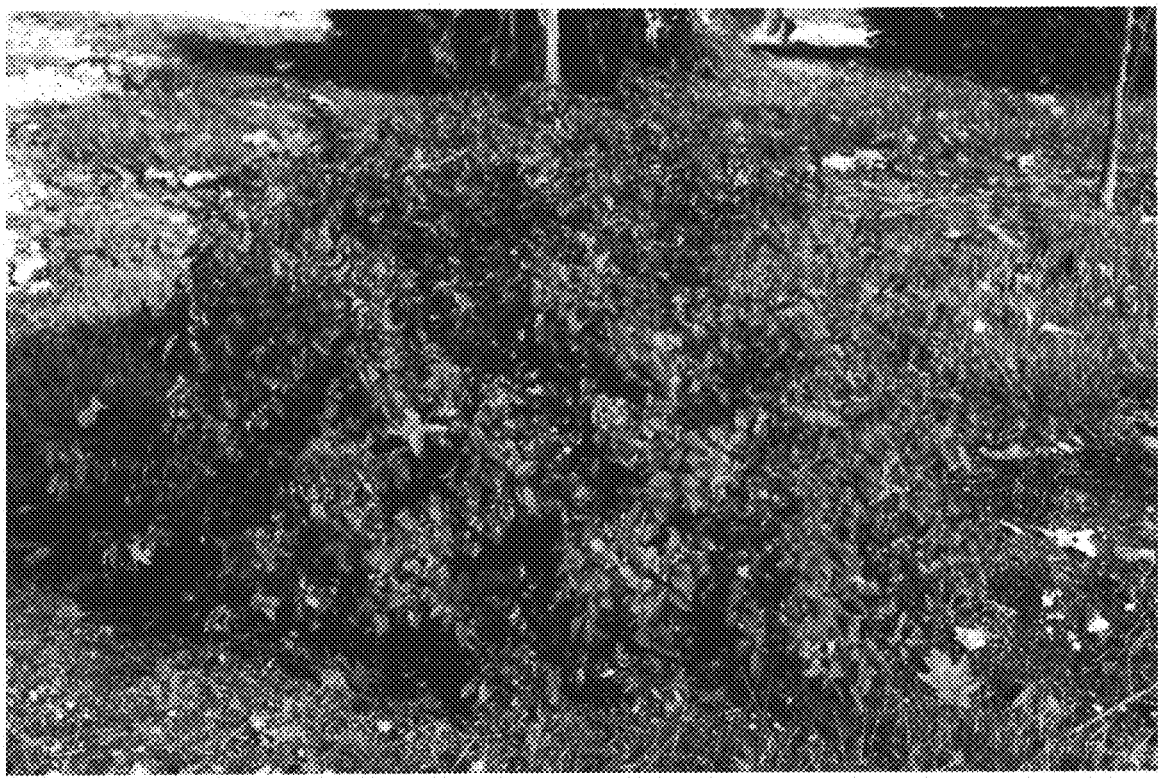

The photograph in FIG. 4 provides a view of the fall foliage colors of a 12-year-old plant of 'JN Select J'.

The colors in the photographs are as close as possible with the digital photography techniques available, the color values cited in the detailed botanical description accurately describe the colors of the new *Spiraea.*

DETAILED BOTANICAL DESCRIPTION

The following is a detailed description of two-year-old plants of the new cultivar as grown outdoors in 2-gallon containers in St. Paul, Minn. with the flower data collected on plants 6 years in age as grown outdoors in the ground in St. Paul, Minn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Average of 4 weeks from late spring to early summer in Wisconsin.

*Plant type.*—Deciduous shrub.

*Plant habit.*—Mounded.

*Height and spread.*—An average of 30 cm in height and 37 cm width as grown in a 2-gallon container, reaches 1.07 m in height by 1.52 m in width as a mature plant in the landscape.

*Hardiness.*—At least in U.S.D.A. Zones 3 to 7.

*Diseases and pests.*—No susceptibility or resistance to diseases or pests has been observed.

*Root description.*—Fibrous and fine, N199D in color.

*Root development.*—Average of 3 to 4 weeks for root initiation, 8 to 10 weeks to fully root in a 1-quart container by direct sticking multiple cuttings.

*Growth rate.*—Vigorous for a *Spiraea.*

Branch description:

*Branch shape.*—Rounded.

*Branch color.*—New growth; 145C in spring and becoming 144A suffused with 164A and 183A in summer, turning to 166A in fall, mature wood; 165B, trunk; 165A.

*Branch size.*—Main branches; an average of 12 cm in length and 3 mm in width, lateral branches; an average of 13 cm in length and 2 mm in width, trunk; 2 cm in length and 1.5 cm in width.

*Branch strength.*—Strong.

*Branch surface.*—New growth; slightly glossy and smooth, mature; ribbed surface, slightly glossy to dull, moderately covered with woolly pubescence; average of 0.5 mm in length and ranges between 156D in color to matching stem surface, mature wood and trunk; bark-like, rugose and dull.

*Internode length.*—An average of 2 cm.

*Branching.*—An average of 25 main stems, an average of 12 lateral branches per main stem, stems held upright to outward at multiple angles.

Foliage description:

*Leaf shape.*—Elliptic.

*Leaf division.*—Simple.

*Leaf base.*—Acute.

*Leaf apex.*—Acute.

*Leaf fragrance.*—None.

*Leaf venation.*—Pinnate, upper and surfaces match leaf surface color throughout the seasons.

*Leaf margins.*—Serrated.

*Leaf arrangement.*—Alternate.

*Leaf attachment.*—Petiolate.

*Leaf surface.*—Both surfaces glabrous and dull.

*Leaf size.*—Average of 5 cm in length and 2.5 cm in width.

*Leaf quantity.*—Average of 30 per lateral branch.

*Leaf color.*—Spring and summer: after bud burst; upper surface color a blend of 137A and 143A, lower surface color 191A, as leaves expand developing to a blend of 178A and 146A, young lower surface; a blend of 178A and 146A, mature upper surface 178A, 183A, N186C and 146A, mature lower surface 191A with hints of 178A, fall; upper and lower surface; a vast blend of colors that range between 137A, 145A, 151A, 178A, N186C, 187C, becoming 187C and 46A as the plant ages.

*Petioles.*—Up to 4 mm in length and 1 mm in width, both surfaces dull and glabrous and changes color to match leaf surface colors as the leaf color changes.

Inflorescence description:

*Inflorescence type.*—Dense umbellate corymbs, present at terminus of lateral branches.

*Inflorescence size.*—Average of 12 cm in diameter and 9 cm in depth.

*Peduncles.*—Up to 4 cm in length and 2 mm in width, surface is sparsely covered with matted, woolly pubescence, young; moderately strong, very glossy, color upper surface is 183A, color lower surface is 145A, mature; very strong, slightly glossy, color upper surface is 146A, color lower surface is 148A.

*Pedicels.*—Up to 2 cm in length and 1 mm in width, surface is sparsely covered with matted, woolly pubescence, young; moderately strong, very glossy, color upper surface is 183A, color lower surface is 145A, mature; very strong, slightly glossy, color upper surface is 146A, color lower surface is 148A.

*Flower buds.*—Globose in shape, 2 mm in depth and diameter, before opening; 152A, flushed with 145A, maturing bud before burst; center 63A with sepal edges 69A in color forming a star shape around the center when opening bud changing to a blend of 65A, 65B and 69A.

*Flower fragrance.*—Light and pleasant fragrance.

*Persistence of flowers.*—Calyx persistent.

*Flower quantity.*—Average of 300 per inflorescence.

*Lastingness of inflorescence.*—An average of 12 weeks with individual flowers lasting an average of 2 days.

*Flower type.*—Rotate with numerous extended stamens.

*Flower aspect.*—Inflorescence held upright on stem terminus.

*Flower size.*—Average of 7 mm in diameter and 5 mm in depth.

*Petals.*—5, average of 3 mm in length and width, orbicular in shape, apex is wavy and rounded, rounded base, both surfaces glabrous, color; upper and lower surface when opening 70D and 69B, upper and lower surface when fully open 69C.

*Calyx.*—Cone-shaped with flared tips, average of 2 mm in width and depth.

*Sepals*.—5, tips are an average of 0.5 mm in length and 1 mm in width, fused base, ovate in shape, entire margins, acute apex, surface glabrous on both surfaces, color; 144A, base is translucent and 63A.

Reproductive organs:

*Pistils*.—3, style; 1 mm in length, 68C in color, stigmas; 0.5 mm in diameter, 67A in color, ovaries; superior, oblong in shape, 1.5 mm in length and 0.5 mm in width, 158A in color.

*Stamens*.—Average of 15, showy filaments; up to 6 mm in length and NN155A in color, anthers; 0.3 mm in diameter, 158C in color, pollen; low in quantity, NN155B in color.

*Fruit and seed*.—No seed production has been observed to date and is considered seedless.

It is claimed:

1. A new and distinct cultivar of *Spiraea* plant named 'JN Select J' as herein illustrated and described.

* * * * *